United States Patent [19]

Corbin et al.

[11] Patent Number: 4,720,328
[45] Date of Patent: Jan. 19, 1988

[54] METHOD FOR REMOVING IMPURITIES FROM CAPROLACTAM

[75] Inventors: Tom F. Corbin; Jack A. Dellinger; Kenneth B. Wagener, all of Asheville, N.C.

[73] Assignee: Akzona Incorporated, New York, N.Y.

[21] Appl. No.: 529,063

[22] Filed: Sep. 2, 1983

Related U.S. Application Data

[63] Continuation of Ser. No. 277,522, Jun. 26, 1981, abandoned.

[51] Int. Cl.⁴ .................. C07D 201/16; B01D 3/10; B01D 3/34
[52] U.S. Cl. .......................... 203/37; 203/27; 203/35; 203/36; 540/540
[58] Field of Search .................. 260/239.3 A; 203/29, 203/35, 36, 37; 540/540

[56] References Cited

U.S. PATENT DOCUMENTS

| | | | |
|---|---|---|---|
| 2,667,483 | 1/1954 | Zeegers et al. | 260/239.3 A |
| 2,944,944 | 7/1960 | Clayton | 203/29 |
| 3,016,375 | 1/1962 | Hopkins et al. | 260/239.3 A |
| 3,016,376 | 1/1962 | Hopkins et al. | 260/239.3 A |
| 3,145,198 | 8/1964 | Morbidelli et al. | 260/239.3 A |
| 4,264,501 | 4/1981 | Bour et al. | 203/35 |

OTHER PUBLICATIONS

Stevens "Polymer Chemistry", An Introduction, Addison-Wesley (1975), pp. 281-286.

*Primary Examiner*—Robert T. Bond
*Attorney, Agent, or Firm*—Alan R. Stempel; Jeffrey S. Boone; Jack H. Hall

[57] ABSTRACT

A method for removing impurities from caprolactam is disclosed. The method comprises the sequential steps of treating the impure caprolactam with phosphorus pentoxide so that the impurities react therewith to form high boiling species and then distilling the so treated impure lactam to recover substantially pure caprolactam as overhead, with the impurities remaining as bottoms.

6 Claims, No Drawings

METHOD FOR REMOVING IMPURITIES FROM CAPROLACTAM

RELATED U.S. APPLICATION DATA

This application is a continuation of Ser. No. 06/277,522, filed June 26, 1981, now abandoned.

BACKGROUND OF THE INVENTION

This invention relates to a method for removing impurities and contaminants from caprolactam and, in particular, to a method for removing compounds having hydroxy, amino or carboxyl functional groups from caprolactam.

The production of yarns from polycaproamide, or, more commonly, nylon-6, requires the utilization of ε-caprolactam of substantial purity. Experience has shown that the use of impure lactam often will lead to poor polymerizations and will produce yarn which is, variously, of poor color, brittle, or which decomposes or degrades upon storage. Additionally, impure lactam itself often has an off color, which is not favored in the nylon industry.

While it is, of course, possible for caprolactam to become contaminated with any of a vast number of possible impurities, certain types of contamination are encountered with sufficient frequency to be of commercial concern.

Of foremost concern as a contaminant is ethylene glycol, which may be introduced into lactam in a variety of ways. For example, it is the usual practice to depolymerize waste nylon in order to recover caprolactam, which is rather costly, and to the reuse the recovered lactam as a feedstock for further nylon production. If, as sometimes happens, ethylene glycol derived polyester waste becomes commingled with the nylon, either by accident or design, the resulting stream of depolymerized waste will contain not only caprolactam but also ethylene glycol and terephthalic acid as a result of the depolymerization of the polyester.

Similarly, it is a usual practice to clean nylon 6 polymerization vessels by boiling them with ethylene glycol, which serves to depolymerize deposits in the vessel interior. Failure to adequately purge the glycol so introduced will, of course, cause any nylon produced in the vessel to be contaminated with ethylene glycol. As explained before, the nylon so produced will be subject to various defects. But, further, it is a standard practice to wash chips of freshly polymerized nylon in water in order to recover unreacted lactam and oligomers. Experience has shown that lactam recovered from glycol contaminated nylon chips will itself be contaminated with ethylene glycol. It is easy to see that if this contaminated lactam is then reused as a feedstock, a nylon-6 production line can become chronically contaminated with glycol and that the nylon produced by the line will be of an inferior quality.

Other contaminants may also find their way into caprolactam, although their occurrence may be less common. Thus, contamination by alcohols other than ethylene glycol may occur if lactam is recovered through the depolymerization of waste nylon-6 which has been mixed, either purposefully or inadvertently, with polyester derived from such other alcohols, e.g., propylene glycol in the case of polypropylene terephthalate, or butylene glycol in the case of polybutylene terephthalate. And, of course, terephthalic acid contamination will also result from the depolymerization of these polyesters, as in the case of the depolymerization of polyethylene terephthalate polyester. Contamination by compounds having both amino and carboxyl functional groups may occur, for example, if nylon-6 waste is mixed with nylon-66 and then depolymerized, the depolymerization of nylon-66 yielding hexamethylenediamine and adipic acid.

Although prior inventors have presented methods for removing various contaminants from caprolactam, most notably alkalene glycols such as ethylene glycol, it is believed that none of these prior methods is entirely satisfactory.

Accordingly, it is a general object of this invention to provide a method for removing impurities from caprolactam so as to yield a product of exceptional purity.

It is a more specific object to provide a method for removing impurities from caprolactam which fall within the class of compounds comprising hydroxy, amino or carboxyl functional groups.

A still more specific object is to provide a method for removing alkalene glycols, particularly ethylene glycol, from caprolactam.

Another specific object of the invention is to provide a method for removing color causing impurities from caprolactam.

And, as further objects, the invention is intended to provide a method for removing impurities from caprolactam which is both suitable for use on a large scale and economical.

DESCRIPTION OF THE INVENTION

In accordance with the foregoing objects, it has now been discovered that various compounds comprising either hydroxy, amino or carboxyl functional groups may be removed from caprolactam by a method which comprises the sequential steps of: treating the lactam with phosphorus pentoxide so that the contaminants react with the phosphorus pentoxide to form species which are substantially non-volatile with respect to caprolactam and distilling the so treated impure caprolactam to recover substantially pure lactam as overhead, with said reacted impurities remaining as bottoms. In order to maximize the yield of the purification, it is preferable to add a method step prior to the addition of phosphorus pentoxide wherein the water content of the lactam is reduced so that it does not exceed about 0.2 weight percent. Also, optionally, but preferably, two additional method steps are added, which comprise: treating the thus purified lactam with a suitable alkaline neutralizing substance, such as calcium hydroxide, to reduce its free acid content; and distilling the thus treated lactam once again to separate the lactam from the reacted alkaline substance. This method has been found suitable for use not only on a small laboratory scale, but in the large scale commercial reclamation of caprolactam as well.

While not wishing to be bound by any particular theory, it is believed that phosphorus pentoxide is capable of acting, in the case of alcohols, to yield phosphate esters; in the case of amines, to yield phosphate amides; and in the case of carboxylic acids, to yield mixed anhydrides. Indeed, we have found that in the purification of lactam containing ethylene glycol, the bottoms remaining after distillation can be hydrolyzed to yield glycol. While no attempt has been made to determine the structures of the non-volatile phosphates formed, it is assumed that several competing reactions can take place to yield a mixture of various phosphates compounds.

In order to assure substantially complete removal of contaminant from the lactam, it is preferred to use at least a stoichiometric equivalent of phosphorus pentoxide. Thus, for example, in the case of caprolactam contaminated by 1 weight percent of ethylene glycol, 3 weight percent, or slightly more than an equimolar amount, of phosphorus pentoxide has been found to substantially completely react with and effectively remove the glycol. Provided that the reaction temperature is above the melting point of caprolactam, the temperature at which the phosphorus pentoxide is reacted with the contaminant does not appear to be critical, although somewhat elevated temperatures are preferred, since the reaction proceeds more rapidly. In this regard, we have found it advantageous to conduct the reaction by refluxing the lactam with phosphorus pentoxide prior to distillation, which is typically carried out at 140° C. under vacuum.

In order to maximize the yield, it is preferable, but not necessary, in performing the method of the invention, to reduce the water content of the lactam to less than about 0.2 percent prior to the addition of phosphorus pentoxide. If this is not done, the phosphorus pentoxide reacts with water to yield phosphoric acid which catalyzes the polymerization of lactam, leading to the formation of oligomers and greatly reducing the effectiveness of glycol removal. Simple evaporation and subsequent distillation may conveniently be employed to remove the requisite amount of water.

The actual separation of caprolactam from the reacted contaminants may be accomplished by typical distillation techniques. For example, laboratory scale purifications have been run using simple vacuum distillation from a pot at 140° C. while production scale distillations have been performed using wiped film evaporators.

Finally, lactam purified by the method of the invention usually has an unacceptably high free acid content. If stored, this high free acid content lactam discolors and produces an off color polymer. Accordingly, to reduce this free acid content, we have found it a good practice to further process the lactam by neutralizing the acid with an alkaline substance, for example, calcium hydroxide, and then effecting a further distillation.

Using the above described procedure, lactam of exceptionally high purity and good color may be obtained in high yield.

Having thus generally described the invention, reference will be made to the accompanying Examples thereof.

EXAMPLE I

Four samples of ε-caprolactam, each contaminated with 1.0 percent of ethylene glycol, based upon the weight of lactam, were treated with 1.0, 2.0, 3.0 and 5.0 weight percent of phosphorus pentoxide, respectively, for a short period (about 30 minutes) at 90° C. The treated samples were then each distilled under vacuum at 140° C. and the lactam recovered as overhead. The percent of ethylene glycol contamination remaining in each sample upon the completion of the above procedure, as determined by gas chromatography, is given in Table I, below. It will be seen that substantially complete removal of glycol was effected using 3 weight percent of phosphorus pentoxide, or slightly in excess of an equimolar amount.

TABLE I

| $P_2O_5$ TREATMENT OF LACTAM CONTAMINATED WITH 1% GLYCOL | |
|---|---|
| Wt. % $P_2O_5$ Added | Results (Wt. % EG in Lactam) |
| 1.0 | 400 ppm |
| 2.0 | 100 ppm |
| 3.0 | <50 ppm |
| 5.0 | <50 ppm |

EXAMPLE II

In order to demonstrate the feasibility of large scale lactam purification, a 30,000 pound sample of caprolactam containing about 5 percent (5%) water and contaminated with about 2,000 ppm ethylene glycol was charged into the feed tank of a wiped film evaporator equipped with both lactam and water condensers and circulated through the unit until the water content was lowered to less than 0.2 percent. Then 600 pounds (2 percent by weight of lactam) of phosphorus pentoxide was added to the feed tank by means of a screw conveyor and distillation was started with the distillate being returned to the feed tank for the first 30 minutes to allow complete reaction of the glycol. After 30 minutes, the lactam distillate was taken off the lactam condenser, valved to an alternate feed tank, and the distillation allowed to proceed. As the lactam was removed, the viscosity of the residual feed material was found to increase. Accordingly, when about 85 to 90 percent of the lactam had been removed, the bottoms were no longer returned to the feed tank, but were cast off and the feed flow was concommitantly reduced. At this point, the process yield of lactam was about 90 to 95 percent. Next, in order to eliminate the free acid content of the recovered lactam, about 15 gallons of water and enough calcium hydroxide to neutralize the acid was added to the lactam in the alternate feed tank and the contents of the tank agitated to assure complete reaction. Then, a final distillation was effected using the wiped film evaporator, in order to remove the calcium hydroxide, with the purified lactam being taken off of the lactam condenser and valved to a collection tank. The final yield of the process was about ninety percent (90%). An analysis of the lactam so recovered is given in Table II below.

TABLE II

| ANALYSIS OF PURIFIED CAPROLACTAM | |
|---|---|
| Property | Value |
| Moisture | .2% |
| Color APHA | 5 |
| Permanganage Number | 24 |
| Free Base | .12 meq/kg |
| Volatile Base (as $NH_3$) | 13 ppm |
| Glycol | 20 ppm |
| Phosphorus (as $PO_4$) | 7 ppm |

EXAMPLE III

Lactam contaminated with about 0.5 weight percent of ethylene glycol and 1.45 weight percent of terephthalic acid is reacted with about 3.0% w/w of phosphorus pentoxide at 80° C. for a short period and then distilled at 140° C. at reduced pressure. The resulting intermediate lactam is treated with calcium hydroxide and again distilled. The thus purified caprolactam should be found to be substantially free of glycol, terephthalic acid and any other free acid.

EXAMPLE IV

Lactam contaminated with about 0.93 weight percent of hexamethylenediamine and 1.17 weight percent of adipic acid is reacted with about 3.0% w/w of phosphorus pentoxide at 80° C. for a short period and then distilled at 140° C. at reduced pressure. The resulting intermediate lactam is treated with calcium hydroxyde and again distilled. The thus purefied caprolactam should be substantially free of both hexamethylenediamine, adipic acid and any other free acid.

While the invention has been described with reference to certain specific examples and illustrative embodiments, it is, of course, not intended to be so limited except insofar as appears in the accompanying claims.

We claim:

1. A method for removing impurities from ε-caprolactam containing less than about 0.2% (wt.) of water which comprises the sequential steps of:
   (a) treating said impure caprolactam with phosphorus pentoxide so that said impurities react with said phosphorus pentoxide to form species which are substantially non-volatile with respect to caprolactam; and
   (b) distilling the so treated impure caprolactam to recover substantially pure caprolactam as overhead, with said reacted impurities remaining as bottoms.

2. The method of claim 1 wherein said impurities are selected from the class of compounds comprising hydroxy, amino or carboxyl functional groups.

3. The method of claim 1 wherein said impurity is ethylene glycol.

4. The method of claim 1 wherein at least a stoichiometric equivalent of phosphorus pentoxide is used, based upon the concentration of impurity in said lactam.

5. The method of claim 1 comprising the additional steps of:
   (a) after said distillation step, treating said recovered lactam with a sufficient amount of an alkaline substance to neutralize any free acid present therein; and
   (b) further distilling said lactam to remove said alkaline substance.

6. The method of claim 2, where the substantially non-volatile species comprise, respectively, phosphate esters, amides or mixed anhydrides.

* * * * *